United States Patent [19]

Todd et al.

[11] Patent Number: 4,988,489

[45] Date of Patent: Jan. 29, 1991

[54] RECOVERY OF PHOSPHORUS VALUES FROM WASTE PHOSPHORIC ACID LIQUORS

[76] Inventors: Lanny E. Todd, 7629 Indian Springs Dr., Nashville, Tenn. 37221; Alec F. Bridges, 5007 Criddle Dr., Columbia, Tenn. 38401

[21] Appl. No.: 302,156

[22] Filed: Jan. 25, 1989

[51] Int. Cl.$^5$ .............................................. C01B 25/16
[52] U.S. Cl. ................................ 423/321 R; 423/316; 423/321 S
[58] Field of Search ................. 423/321 R, 321 S, 316

[56] References Cited

U.S. PATENT DOCUMENTS

| | | | |
|---|---|---|---|
| 3,410,656 | 11/1968 | Bunin et al. | 423/321 X |
| 3,739,046 | 6/1973 | Stanford et al. | 423/316 |
| 3,749,047 | 6/1973 | Stanford et al. | 423/316 |
| 4,483,838 | 11/1984 | Sculthorpe | 423/316 |

*Primary Examiner*—Gregory A. Heller
*Attorney, Agent, or Firm*—Paul J. Juettner

[57] ABSTRACT

The phosphorus values from waste phosphoric acid containing organic contaminents such as wastes obtained in the manufacture of quinacridone pigments can be recovered in purified form by hydrolyzing phosphate esters, removing any formed alcohol, dissociating any amine phosphates and separating any free amine. The phosphorus values can be recovered in a purified form as phosphate salts.

20 Claims, No Drawings

RECOVERY OF PHOSPHORUS VALUES FROM WASTE PHOSPHORIC ACID LIQUORS

The present invention relates to the recovery of phosphorus values from waste phosphoric acid streams contaminated with organic materials, particularly those wastes obtained from quinacridone pigment manufacturing.

BACKGROUND OF THE INVENTION

Pigments, such as quinacridone, are well known and can be synthesized by the reaction which is illustrated below:

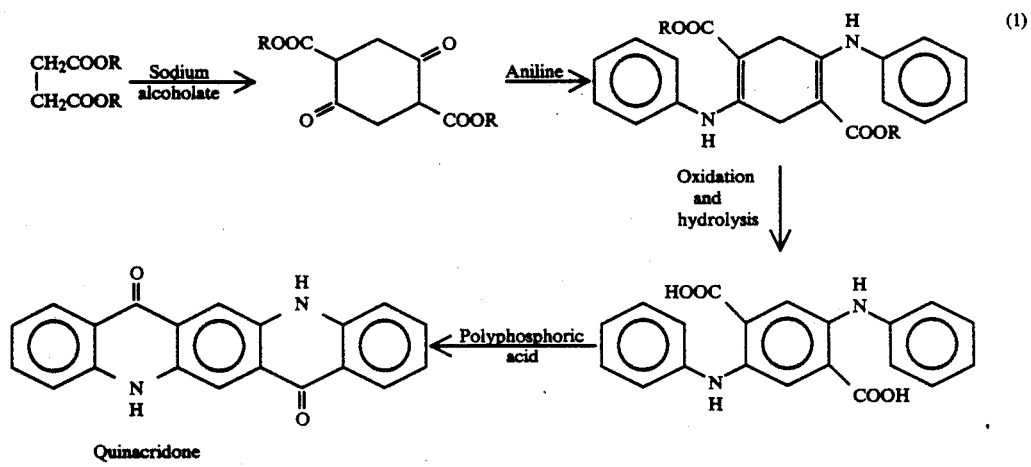

By using amines other than aniline, substituted quinacridones, also having pigmentary characteristics, can be prepared.

As shown above, the last step in the reaction is a ring closing reaction with polyphosphoric acid. The by-product of that step is a phosphoric acid waste stream contaminated with organic materials. Past attempts at purifying the waste phosphoric acid for reuse have met with difficulties.

The purified phosphoric acid that is obtained remains contaminated with organic materials. Heretofore, the only outlet for this waste phosphoric acid has been as fertilizer.

SUMMARY OF THE INVENTION

In accordance with the present invention it has been discovered that the phosphate values from phosphoric acid waste streams containing organic contaminents such as phosphate esters and/or amine phosphates, such as from the manufacture of quinacridone pigments, can be recovered in a purified state with a minimum amount of organic contamination.

DETAILED DESCRIPTION OF THE PRESENT INVENTION

It has been discovered that, during the manufacture of quinacridone, alkyl phosphate esters as well as small amounts of aromatic amine phosphates are produced and are present in the waste phosphoric acid stream. Attempts at recovery and purification of the waste acid have always led to a product containing organic contamination as the recovery processes have not dealt with the actual form of the organic contamination. The discovery of this fact led to the development of processes of the invention which result in reducing the organic contamination.

The following description of the invention will be based on the process of manufacturing quinacridone as outlined in reaction sequence (1). In this reaction sequence and for purposes of this description, the R groups are assumed to be methyl, the sodium alcoholate is based on methanol and the solvent is methanol. The following description is intended to apply equally to other alkyl groups and alcohols in the same process as well as other processes which have an alcohol base and ultimately contain phosphoric acid, phosphate esters and/or amine phosphates. It is also noted that the amine which is added to the system is aniline. The description of the invention will be directed to aniline and to amines in general. It is intended that the description of the invention is applicable to systems containing waste phosphoric acid streams which result from the manufacture of chemical compounds in the presence of alcohols and/or amines and phosphoric acid.

During the manufacture of the quinacridone by the process described in reaction sequence (1), there is formed a phosphoric acid waste stream containing mono-, di- and trimethyl esters of phosphoric acid, amine phosphates and free methanol. The major impurity is monomethyl phosphate with trace amounts of aromatic amine phosphates and di- and triphosphate esters. It has been discovered that the phosphate esters and particularly the monomethyl ester contained in the waste phosphoric acid can be almost completely and easily decomposed by hydrolysis at elevated temperatures as per the following reaction sequence:

$$CH_3OPO(OH)_2 + H_2O \rightarrow H_3PO_4 H_3PO_4 + CH_3OH \quad (2)$$

Any method of effecting the hydrolysis of the phosphate esters can be used such as by heating the acid to a temperature and for a time sufficient to effect the hydrolysis. Hydrolysis temperatures are dictated by practical considerations. Below about 70° C. the hydrolysis proceeds too slowly to form the basis of a practical commercial system. Above about 150° C., the acid is corrosive to most economical metal reactors and its temperature exceeds the practical upper limits for using glass lined reactors. Preferably, the acid is heated to and maintained at boiling to effect the hydrolysis.

Decomposition of the monomethyl phosphate can be effected by refluxing the acid for a given time at elevated temperature. Methanol can then be removed by stripping.

Depending on the composition of the waste phosphoric acid, the times and temperatures for hydrolysis can vary. For instance, for an "as is" waste phosphoric acid containing about 60% phosphoric acid and about 16% of the monomethyl phosphate ester and at an effective hydrolysis temperature ranging from about 126°–128° C., eleven hours were required to obtain a decomposition of the methyl phosphate ester of about 74%. If the acid was preconcentrated and at an effective temperature of 148°–153° C., it was found that 96% decomposition could be obtained in about 23 hours.

If there is adequate water in the acid to effect the hydrolysis, then no additional water need be added. However, additional water can be added, if such is necessary.

The methanol in the acid resulting from the hydrolysis and free methanol is desirably removed from the system to the extent possible by any appropriate means. Steam stripping has been found to be an effective and desirable means for removing the methanol leaving a phosphoric acid with only trace amounts of methyl esters and the amine phosphates present. Upon stripping of the alcohol, additional water can be added to maintain the fluid volume in the reactor at a practical level and control the boiling temperature.

If complete removal of the monoester is required and/or a short processing time is necessary, then simultaneous hydrolysis and stripping is dictated. It has been found that the hydrolysis reaction shown in reaction sequence (2) is reversible in the presence of large amounts of free methanol. The presence of free methanol results in a very slow net decomposition of the methyl phosphate ester. This has been overcome by the simultaneous hydrolysis and stripping of the methanol. Water is added to maintain the reaction volume while volatilizing the methanol. It has been found that simultaneous hydrolysis and stripping for 5 utilizing the "as is" phosphorus acid waste (not preconcentrated) as described above, decomposes 99.5% of the monomethyl phosphate ester after 5 hours versus only 74% after 11 hours.

It is expected that the dimethyl and possibly the trimethyl esters can also be effected by these procedures.

The product obtained after hydrolysis and, preferably, after stripping of the methanol, can be used as is or processed further. If amines were present in the initial reaction, the product can contain amine phosphates contaminants as these have not as yet been isolated or removed.

It has been found that when the pH of the acid is increased sufficiently, the amine phosphate dissociates and free amine is formed. For example, within a pH range of about 4.2 to about 4.5 for aniline, essentially all of the aromatic amine exists in the free state. If the free amines are insoluble, they can be removed by filtration or other appropriate means. If dissolved, the amines can be removed by any appropriate means such as by adsorption on activated carbon. Heating during the adsorption step is desirable to speed the purification. The pH necessary to form the free amine compounds may vary between amines. The appropriate pH that is effective to form the free amine compounds can easily be determined by one of ordinary skill in the art.

As the product obtained from the neutralization of the acid is a phosphate salt, selection of the base will be dictated by the final salt desired. Basic materials such as sodium, potassium and ammonium hydroxides and carbonates as well as anhydrous ammonia can be used. Monobasic, dibasic and tribasic salts such as monoammonium phosphate (MAP) and trisodium phosphate (TSP) can be formed depending on the base and amount used. The free acid can also be regenerated by treatment with an ion exchange resin.

Upon formation of the free amine, the amine can be separated if in solid form or made into solid form by appropriate chemical treatment. If the amine is in solution, the phosphate values can be separated without separation of the amine. Preferably, the soluble amine is separated prior to separating the phosphorus values. Any appropriate separation means can be used such as adsorption on activated carbon. Heating may be required for effective adsorption.

In one of the preferred embodiments anhydrous ammonia is used to form monoammonium phosphate while liberating the amine. Upon removal of the amines, the monoammonium phosphate (MAP) can be recovered by appropriate means such as crystallization. The exact method of treating the solution to remove the amines and to effect crystallization are easily determined by one of ordinary skill in the art. By this procedure, monoammonium phosphate with little organic contamination can be obtained.

It has also been found that salts, such as trisodium phosphate (TSP) or tripotassium phosphate (TPP), can be prepared by omitting the hydrolysis of the phosphate esters since the esters can be saponified during the process. This is clearly shown in reaction sequences (3) and (4):

$$CH_3OPO(OH)_2 + 3.2NaOH + 10H_2O$$

$$Na_3PO_4 \cdot 12H_2O\text{-}0.2NaOH + CH_3OH \qquad (3)$$

$$H_3PO_4 + 3.2NaOH + 9H_2O$$

$$Na_3PO_4 \cdot 12H_2O\text{-}0.2NaOH \qquad (4)$$

If iron salts are present in the acid, they will precipitate as the hydroxide. As can be seen from the reaction sequence (3) and (4), the waste acid is combined with sodium hydroxide in a diluted state. Alcohol can be removed by stripping. The product can be filtered to remove any precipitate. The temperature is preferably sufficient to maintain the sodium phosphate in solution (about 65.). Means are then used to remove any dissolved free amine such as by adsorption on activated carbon. The trisodium phosphate can then be separated by any normal means such as crystallization.

Any methanol in the reaction mixture can be removed by any appropriate means prior to the removal of the amine. Steam stripping has been found to be an effective means. The removal of the methanol is necessary to minimize the organic contamination of the final trisodium phosphate.

The phosphates prepared by the processes of the present invention can be used in any known areas of those types of compounds. If the degree of purity of the product obtained may not be sufficient to allow food grade use, the compounds can find effective use in the industrial area.

The present invention finds use in recovering the phosphate values from a waste phosphoric acid stream such as formed by the use of polyphosphoric acid in a ring closing reaction of the type used in quinacridone manufacture. The present invention can also find use in recovering the phosphate values from waste phosphoric acid systems containing phosphate ester and/or other phosphate amines.

The present invention will be more fully illustrated in the Examples which follow.

EXAMPLE 1

In a round-bottom 3-neck flask fitted with an electric heating mantle, a magnetic stirrer, a condenser, an addition funnel and a condensate receiver were placed 740 grams (500 milliliters) of a waste acid from the manufacture of quinacridone having about 60% $H_3PO_4$ and about 16% monomethyl phosphate ester ($CH_3OPO(OH)_2$) The following conditions were maintained.

| TIME (MIN) | COMMENTS | TEMP OF LIQUID °C. | TEMP OF VAPOR °C. | % MONOESTER IN HYDROLYZED PROD. |
|---|---|---|---|---|
| 0 | Reflux began | 128 | 97 | — |
| 15 | — | 135 | 100 | — |
| 20 | Began slow Addition of $H_2O$ to hold temp. at 140–145° C. while simulataneously distilling methanol | 140 | 100 | — |
| 140 | — | 143 | 100 | 2.80 |
| 260 | — | 140–145 | 100 | 0.30 |
| 325 | —. | 145 | 100 | 0.08 |

The product contained 79% (±0.5%) $H_3PO_4$ and 0.08% monomethyl phosphate. Thus, 99.5% of the monomethyl ester was decomposed. 35.8 grams of methanol were found in the distillate for a recovery of 108.5% based on the monomethyl ester.

EXAMPLE 2

Manufacture of MAP/Removal of Aromatic Amines 666 grams of purified acid from Example 1 (amber color) were treated with sufficient anhydrous ammonia to elevate the pH to 4.5. After reaching this pH, 7.9 grams of granular activated carbon were added and the temperature was raised to and maintained within the range of 80°–90° C. for one hour. The liquor was filtered hot, obtaining a water-white filtrate, and allowed to cool to room temperature while being stirred. The MAP crystals were separated by filtration and dried in a convection oven at 70° C. There was obtained 442 grams of unwashed crystals. Analysis of the crystals gave a monomethyl phosphate content of 150 ppm and a COD (Chemical Oxygen Demand) of 772 ppm, roughly equal to a total organic carbon content (TOC) of 180 ppm. A MAP having an assay greater than 99.9% was produced.

EXAMPLE 3

Manufacture of Trisodium Phosohate 207 grams of waste phosphoric acid from a manufacturer of quinacridone pigments containing approximately 60% phosphoric acid and about 16% monomethyl phosphate was diluted with deionized water to a total mass of 427.2 grams. Sodium hydroxide beads in an amount of 183 grams were dissolved in deionized water to give a total of 554.5 grams of solution. The diluted acid was slowly added to the sodium hydroxide solution with stirring. After the addition was complete, the liquor was filtered hot at about 65° C., and 20.6 grams of granular activated carbon were added to the filtrate. The slurry was agitated and maintained at about 65° C. for 15 minutes. The slurry was then filtered, the filtrate being essentially water-white. This hot filtrate, containing TSP, was allowed to cool to room temperature while being slowly agitated. The crystals that precipitated were separated by filtration, and were allowed to dry in the air. The analysis of the unwashed crystals was as follows:

| | |
|---|---|
| % $P_2O_5$ | 18.58 |
| Assay calculated from % $P_2O_5$, % $Na_3PO_4.12H_2O.0.2$ NaOH | 101.66 |
| % L.O.I. | 55.75 |
| ppm Fe | 0.4 |
| ppm TOC | 560. |

By this procedure an industrial grade trisodium phosphate product containing low quantities of organic contaminants can be manufactured from a waste phosphoric acid stream. No attempt was made to separate any methanol produced by the saponification of the methyl phosphate esters contained in the raw material stream. Any appropriate means such as steam stripping can be used to remove any or substantially all of the alcohol and minimize contamination of the trisodium phosphate.

What is claimed is:

1. A process for purifying waste phosphoric acid containing alkyl phosphate esters comprising hydrolyzing the alkyl phosphate esters at a temperature and for a time sufficient to effect hydrolysis to form phosphoric acid and alcohol and separating the so formed alcohol from the phosphoric acid.

2. A process for purifying waste phosphoric acid as recited in claim 1 wherein said waste phosphoric acid results from a process for producing quinacridone pigments.

3. A process for purifying waste phosphoric acid as recited in claim 1 wherein the ester is heated to a temperature ranging from about 70° C. to about 150° C.

4. A process for purifying waste phosphoric acid as recited in claim 1 wherein the ester is heated to refluent temperature above 100° C.

5. A process for purifying waste phosphoric acid as recited in claim 1 wherein the process includes the further step of stripping the alcohol from the phosphoric acid by steam stripping.

6. A process for purifying waste phosphoric acid as recited in claim 5 wherein the alcohol is simultaneously hydrolyzed and stripped by steam stripping.

7. A process for removing amines from waste acidic phosphoric acid solutions having a pH sufficient to form amine phosphates comprising elevating the pH to an acidic pH sufficient to dissociate the amine from the phosphate forming free amine and phosphate salts separating the free amine.

8. A process for recovering amines from waste phosphoric acid as recited in claim 7 wherein the amine is aniline, the pH is elevated to a pH ranging from about 4.2 to about 4.5 to form the free amine and is separated by filtration or adsorption on activated charcoal.

9. A process for recovering the phosphorus values in a purified form from a waste phosphoric acid stream containing contaminants of alkyl phosphate esters and amine phosphates comprising:
(a) hydrolyzing the alkyl phosphates at a temperature and for a time sufficient to effect hydrolysis to form phosphoric acid and an alcohol;
(b) separating the alcohol from the phosphoric acid;
(c) adjusting the pH of the acid solution of step (b) to a pH sufficient to dissociate the amine phosphate forming free amine;
(d) separating the amine; and
(e) recovering the phosphorus values the form of phosphate salts.

10. A process for recovering the phosphorus values as recited in claim 9 wherein the waste phosphoric acid stream is the by-product of the manufacture of quinacridone pigments.

11. A process for recovering the phosphorus values as recited in claim 9 wherein the alkyl phosphate esters are hydrolyzed by heating to a temperature above about 70° C. for a period of time sufficient to hydrolyze the esters.

12. A process for recovering the phosphorus values as recited in claim 9 wherein the alcohol is removed by steam stripping.

13. A process for recovering the phosphorus values as recited in claim 9 wherein the phosphate ester is hydrolyzed and the alcohol simultaneously stripped.

14. A process for recovering the phosphorus values as recited in claim 9 wherein the pH is adjusted with a compound selected from the group consisting of sodium hydroxide, sodium carbonate, potassium hydroxide, potassium carbonate, ammonium hydroxide and ammonia.

15. A process for recovering the phosphorus values as recited in claim 9 wherein the free amine is separated by adsorption on activated carbon.

16. A process for recovering the phosphorus values in purified form from a phosphoric acid waste stream containing alkyl phosphate ester and amine phosphate contaminants comprising reacting the waste phosphoric acid stream with a base under conditions sufficient to saponify the phosphate ester forming free alcohol and dissociate the amine phosphate to form free amine; elevating the temperature sufficient to maintain phosphate salts in solution;
(a) separating the alcohol and the amine from the solution and
(b) recovering the purified phosphorus values as phosphate salts.

17. A process for recovering the phosphorus values as recited in claim 16 wherein the waste phosphoric acid stream is the by-product of the manufacture of quinacridone pigments.

18. A process for recovering the phosphorus values as recited in claim 10 wherein the alcohol is removed by steam stripping.

19. A process for recovering the phosphorus values as recited in claim 16 wherein the pH is adjusted with a compound selected from the group consisting of sodium hydroxide, potassium hydroxide, ammonium hydroxide and ammonia.

20. A process for recovering the phosphorus values as recited in claim 16 wherein the free amine is separated by filtration or adsorption on activated carbon.

* * * * *